(12) United States Patent
Sanderson et al.

(10) Patent No.: US 7,402,168 B2
(45) Date of Patent: Jul. 22, 2008

(54) CUSTOM-LENGTH STENT DELIVERY SYSTEM WITH INDEPENDENTLY OPERABLE EXPANSION ELEMENTS

(75) Inventors: David Sanderson, Burlingame, CA (US); Pablo Acosta, Newark, CA (US)

(73) Assignee: Xtent, Inc., Menlo Park, CA (US)

( * ) Notice: Subject to any disclaimer, the term of this patent is extended or adjusted under 35 U.S.C. 154(b) by 443 days.

(21) Appl. No.: 11/104,305

(22) Filed: Apr. 11, 2005

(65) Prior Publication Data
US 2006/0229700 A1 Oct. 12, 2006

(51) Int. Cl.
*A61F 2/06* (2006.01)
(52) U.S. Cl. .................................. 623/1.11; 604/101.01
(58) Field of Classification Search .............. 604/97.01, 604/99.01–99.03, 96.01, 101.01, 101.05; 606/108, 192, 194; 623/1.11, 1.12, 1.16, 623/1.23
See application file for complete search history.

(56) References Cited

U.S. PATENT DOCUMENTS

| | | | |
|---|---|---|---|
| 4,468,224 A | 8/1984 | Enzmann et al. | |
| 4,512,338 A | 4/1985 | Balko | |
| 4,564,014 A | 1/1986 | Fogarty et al. | |
| 4,580,568 A | 4/1986 | Gianturco | |
| 4,681,110 A | 7/1987 | Wiktor | |
| 4,733,665 A | 3/1988 | Palmz | |
| 4,739,762 A | 4/1988 | Palmz | |
| 4,762,129 A | 8/1988 | Bonzel | |
| 4,775,337 A | 10/1988 | Van Wagener et al. | |
| 4,776,337 A | 10/1988 | Palmz | |
| 4,886,062 A | 12/1989 | Wiktor | |
| 4,988,356 A | 1/1991 | Crittenden et al. | |
| 4,994,066 A | 2/1991 | Voss | |
| 4,994,069 A | 2/1991 | Ritchart et al. | |

(Continued)

FOREIGN PATENT DOCUMENTS

EP 0 203 945 B2 12/1986

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner*—Darwin P. Erezo
*Assistant Examiner*—Dianne Dornbusch
(74) *Attorney, Agent, or Firm*—Townsend and Townsend and Crew LLP; J. Grainger, Esq.

(57) ABSTRACT

A stent delivery system for delivering a plurality of stent segments to at least one treatment site includes a catheter shaft having a proximal end and a distal end, a plurality of expandable members arranged axially along the catheter shaft near the distal end, a plurality of stent segments, and a selecting mechanism adapted for selecting one or more expandable members for expansion. Each expandable member is expandable independently of at least one other expandable member, and each expandable member has at least one stent segment positioned on it. One or more of the expandable members may be selectively expanded to deploy the one or more stent segments positioned thereon at the treatment site.

10 Claims, 9 Drawing Sheets

U.S. PATENT DOCUMENTS

| | | | |
|---|---|---|---|
| 5,013,318 A | 5/1991 | Spranza, III | |
| 5,040,548 A | 8/1991 | Yock | |
| 5,092,877 A | 3/1992 | Pinchuk | |
| 5,102,417 A | 4/1992 | Palmz | |
| 5,104,404 A | 4/1992 | Wolff | |
| 5,135,535 A | 8/1992 | Kramer | |
| 5,195,984 A | 3/1993 | Schatz | |
| 5,217,495 A | 6/1993 | Kaplan et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau et al. | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A | 6/1997 | Fischell et al. | |
| 5,662,675 A | 9/1997 | Stockert et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,701 A | 1/1998 | Parodi | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,797,951 A | 8/1998 | Mueller et al. | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,997,563 A | 12/1999 | Kretzers et al. | |
| 6,007,517 A | 12/1999 | Anderson | |
| 6,022,359 A | 2/2000 | Frantzen | |
| 6,033,434 A | 3/2000 | Borghi | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,143,016 A | 11/2000 | Bleam et al. | |
| 6,165,167 A | 12/2000 | Delaloye | |
| 6,179,878 B1 | 1/2001 | Duerig | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,267,783 B1 | 7/2001 | Letendre et al. | |
| 6,273,895 B1 | 8/2001 | Pinchuk et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,325,823 B1 | 12/2001 | Horzewski et al. | |
| 6,357,104 B1 | 3/2002 | Myers | |
| 6,375,676 B1 | 4/2002 | Cox | |
| 6,383,171 B1 | 5/2002 | Gifford et al. | |
| 6,409,753 B1 | 6/2002 | Brown et al. | |
| 6,419,693 B1 | 7/2002 | Fariabi | |
| 6,451,025 B1 | 9/2002 | Jervis | |
| 6,451,050 B1 | 9/2002 | Rudakov et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,511,468 B1 | 1/2003 | Cragg et al. | |
| 6,520,987 B1 | 2/2003 | Plante | |
| 6,527,789 B1 | 3/2003 | Lau et al. | |
| 6,527,799 B2 | 3/2003 | Shanley | |
| 6,555,157 B1 | 4/2003 | Hossainy | |
| 6,575,993 B1 | 6/2003 | Yock | |
| 6,582,394 B1 | 6/2003 | Reiss et al. | |
| 6,592,549 B2 | 7/2003 | Gerdts et al. | |
| 6,599,296 B1 | 7/2003 | Gillick et al. | |
| 6,602,282 B1 | 8/2003 | Yan | |
| 6,605,062 B1 | 8/2003 | Hurley et al. | |
| 6,645,547 B1 | 11/2003 | Shekalim et al. | |
| 6,656,212 B2 | 12/2003 | Ravenscroft et al. | |

| | | |
|---|---|---|
| 6,666,883 B1 | 12/2003 | Seguin et al. |
| 6,679,909 B2 | 1/2004 | McIntosh et al. |
| 6,692,465 B2 | 2/2004 | Kramer |
| 6,699,280 B2 | 3/2004 | Camrud et al. |
| 6,702,843 B1 | 3/2004 | Brown |
| 6,709,379 B1 | 3/2004 | Brandau et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,251 B1 | 6/2004 | Eder |
| 6,800,065 B2 | 10/2004 | Duane et al. |
| 6,849,084 B2 | 2/2005 | Rabkin et al. |
| 7,137,993 B2 | 11/2006 | Acosta et al. |
| 7,147,656 B2 | 12/2006 | Andreas et al. |
| 7,192,440 B2 | 3/2007 | Andreas et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0107560 A1 | 8/2002 | Richter |
| 2002/0111671 A1 | 8/2002 | Stenzel |
| 2002/0138132 A1 | 9/2002 | Brown |
| 2002/0151955 A1 | 10/2002 | Tran et al. |
| 2002/0156496 A1 | 10/2002 | Chermoni |
| 2002/0177890 A1 | 11/2002 | Lenker |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0135266 A1 | 7/2003 | Chew et al. |
| 2003/0139796 A1 | 7/2003 | Seguin et al. |
| 2003/0139797 A1 | 7/2003 | Johnson et al. |
| 2003/0139798 A1 | 7/2003 | Brown et al. |
| 2003/0176909 A1 | 9/2003 | Kusleika |
| 2003/0199821 A1 | 10/2003 | Gerdts et al. |
| 2003/0204238 A1* | 10/2003 | Tedeschi ............ 623/1.11 |
| 2003/0225446 A1 | 12/2003 | Hartley |
| 2004/0024450 A1 | 2/2004 | Shulze et al. |
| 2004/0030380 A1 | 2/2004 | Shulze et al. |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0186551 A1 | 9/2004 | Kao et al. |
| 2004/0215165 A1 | 10/2004 | Coyle et al. |
| 2004/0215312 A1 | 10/2004 | Andreas |
| 2004/0249435 A1* | 12/2004 | Andreas et al. ............ 623/1.12 |
| 2005/0010276 A1 | 1/2005 | Acosta et al. |
| 2005/0038505 A1 | 2/2005 | Shulze et al. |
| 2005/0101624 A1 | 5/2005 | Betts et al. |
| 2005/0125051 A1 | 6/2005 | Eidenschink et al. |
| 2005/0131008 A1 | 6/2005 | Betts et al. |
| 2005/0133164 A1 | 6/2005 | Andreas et al. |
| 2005/0149159 A1 | 7/2005 | Andreas et al. |
| 2005/0209674 A1* | 9/2005 | Kutscher et al. ............ 623/1.11 |
| 2005/0222671 A1 | 10/2005 | Schaeffer et al. |
| 2005/0288763 A1 | 12/2005 | Andreas et al. |
| 2006/0229700 A1 | 10/2006 | Acosta et al. |
| 2006/0229706 A1 | 10/2006 | Shulze et al. |
| 2006/0282147 A1 | 12/2006 | Andreas et al. |
| 2006/0282150 A1 | 12/2006 | Olson et al. |

FOREIGN PATENT DOCUMENTS

| | | |
|---|---|---|
| EP | 0 274 129 | 7/1988 |
| EP | 0 282 143 | 9/1988 |
| EP | 0 505 686 | 9/1992 |
| EP | 0 533 960 | 3/1993 |
| EP | 714640 A1 * | 6/1996 |
| EP | 0 596 145 | 5/1997 |
| EP | 0 947 180 | 10/1999 |
| EP | 1 523 959 | 4/2005 |
| EP | 1 523 960 | 4/2005 |
| EP | 1 266 638 B1 | 10/2005 |
| WO | WO 96/33677 | 10/1996 |
| WO | WO 97/46174 | 12/1997 |
| WO | WO 97/48351 | 12/1997 |
| WO | WO 99/01087 | 1/1999 |
| WO | WO 00/15151 A1 | 3/2000 |
| WO | WO 00/32136 A1 | 6/2000 |
| WO | WO 00/41649 | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 A1 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

Stimpson et al., Parallel Production of Oligonucleotide Arrays Using Membranes and Reagent Jet Printing, BioTechniques 25:886-890 (Nov. 1998).

* cited by examiner

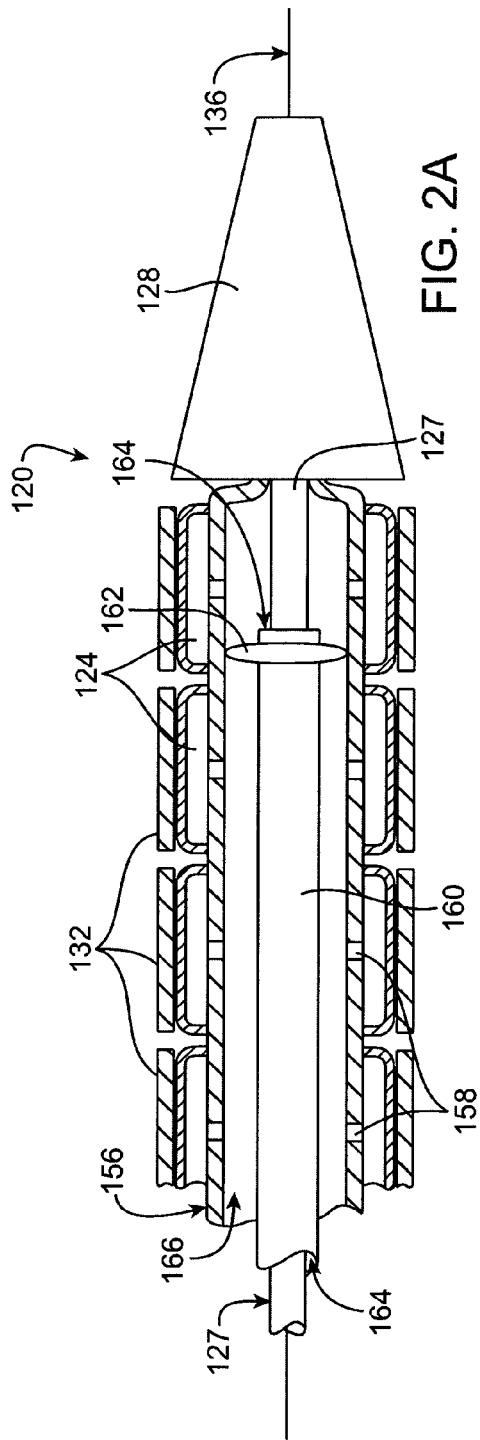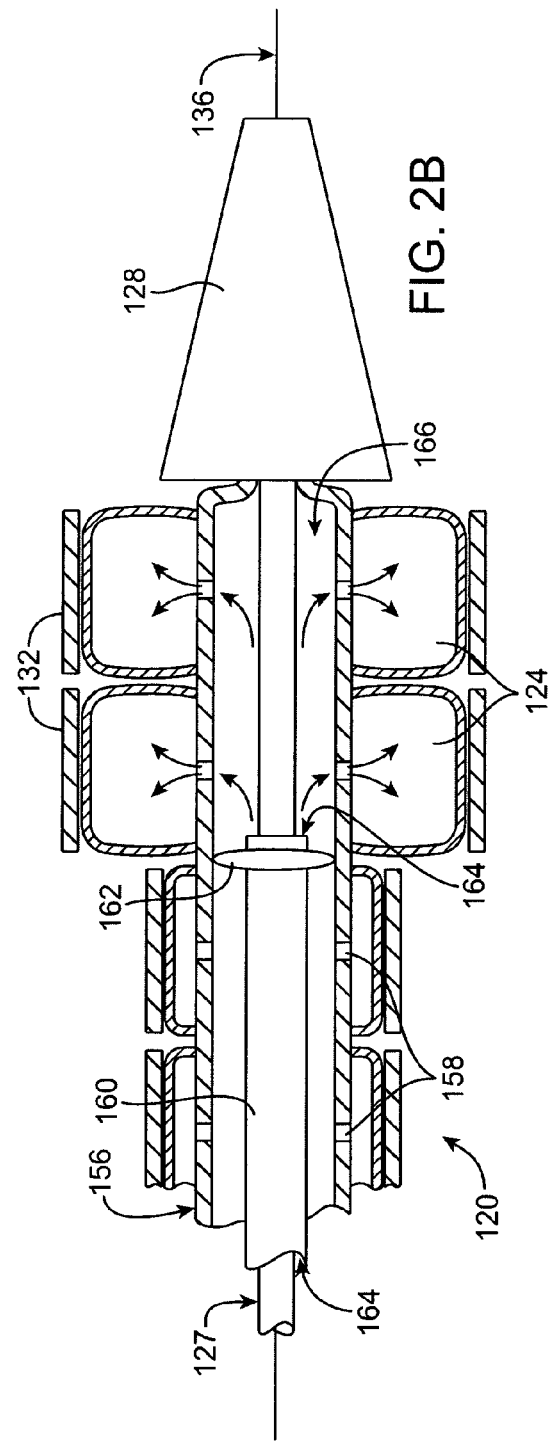

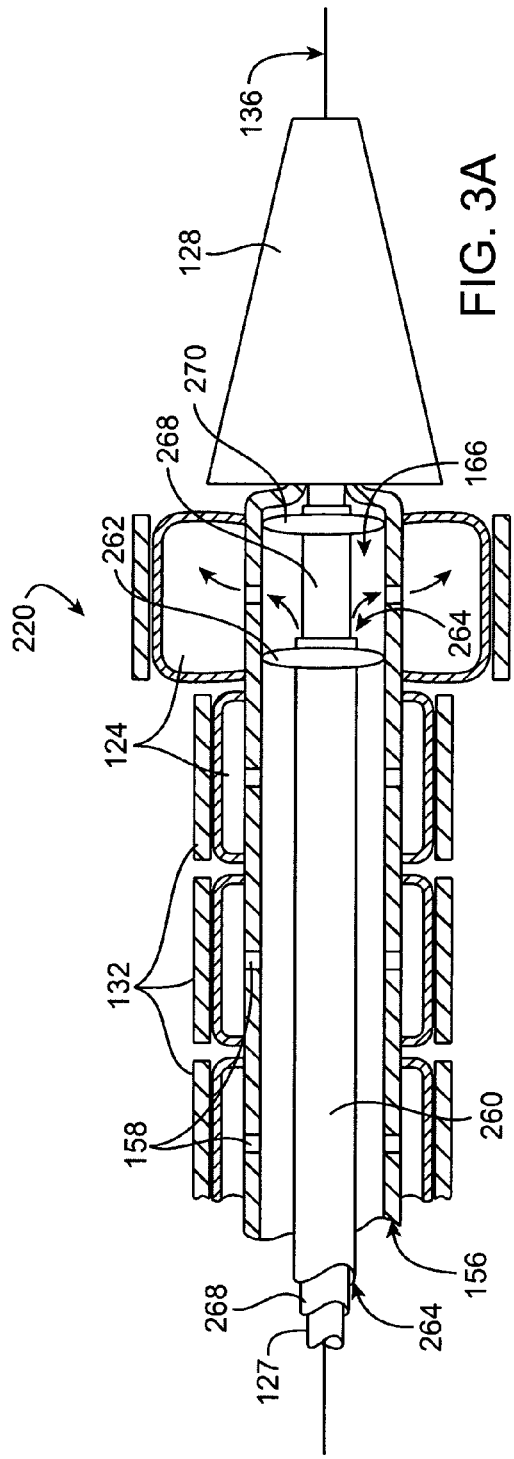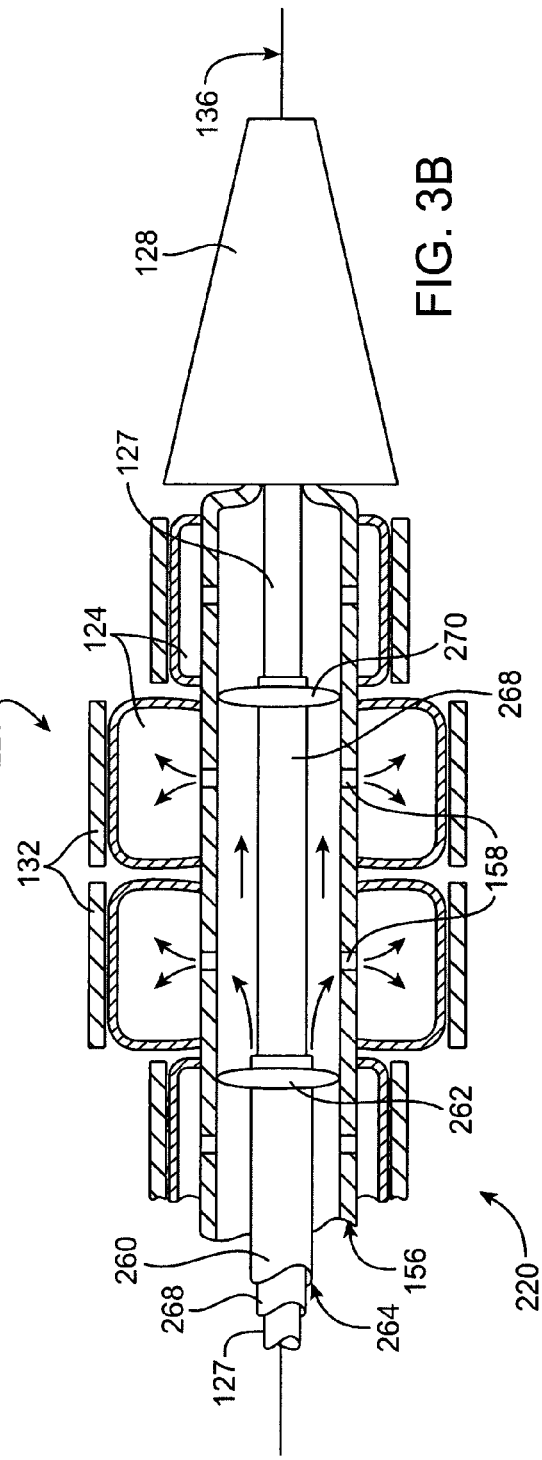
FIG. 3A
FIG. 3B

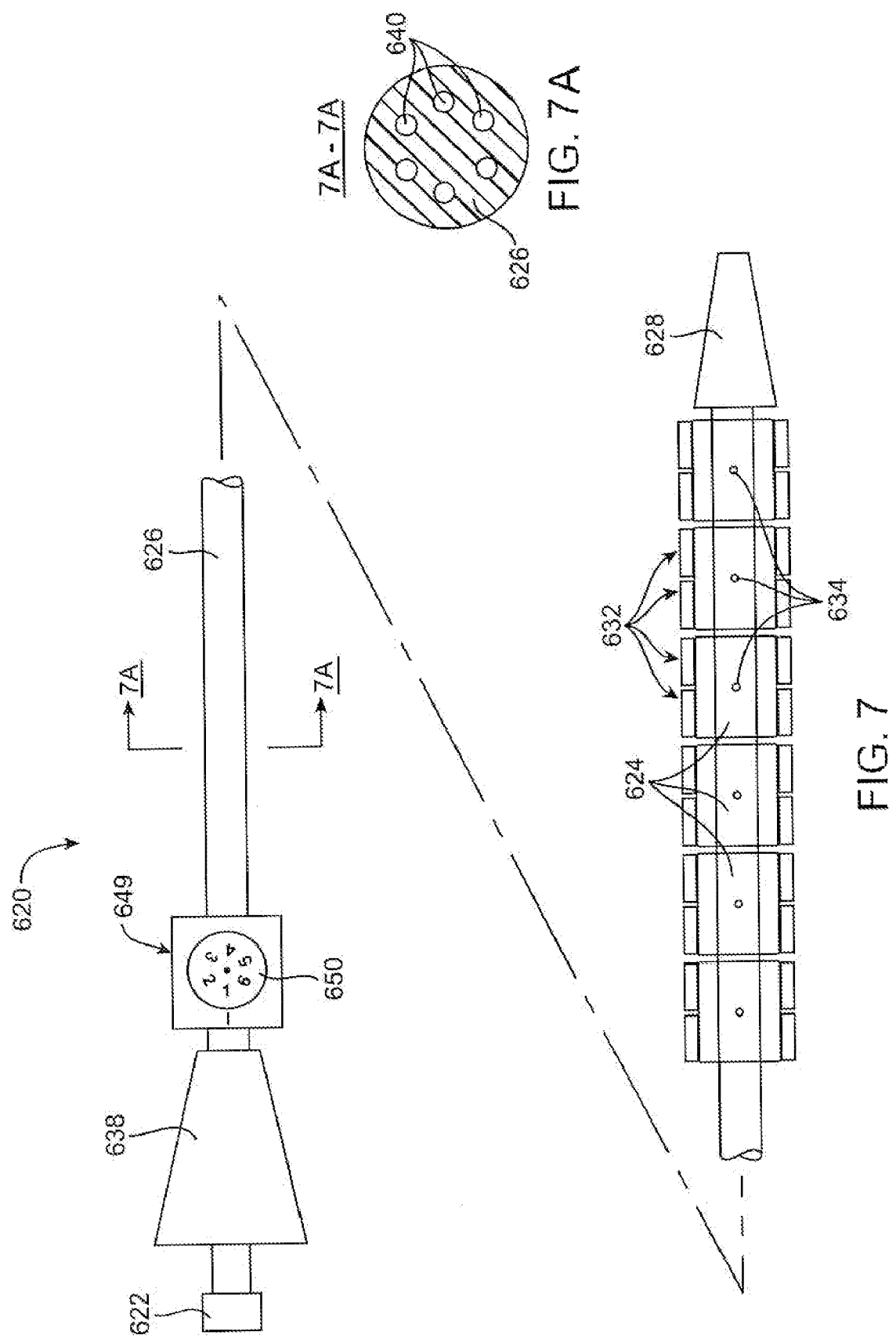

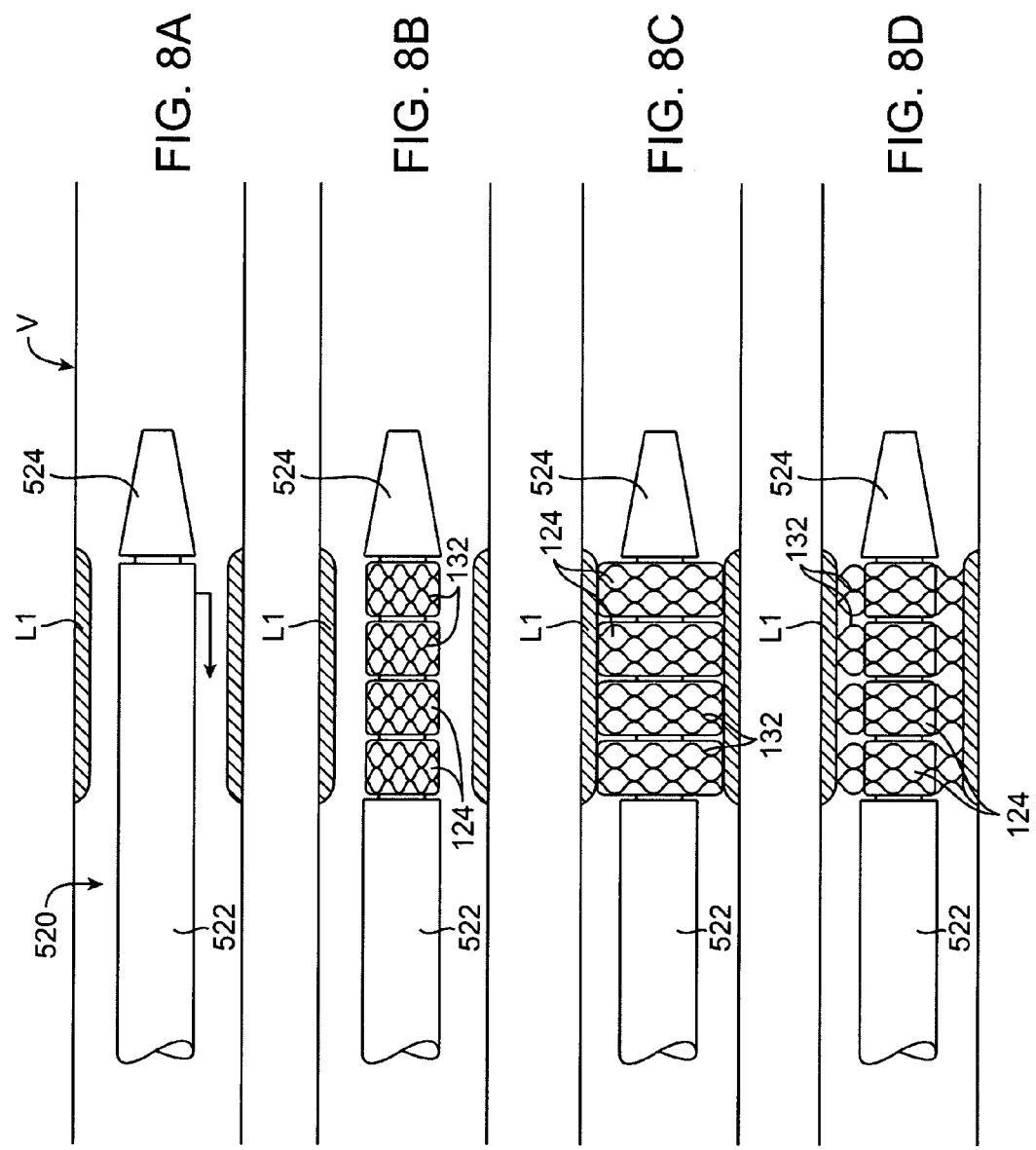

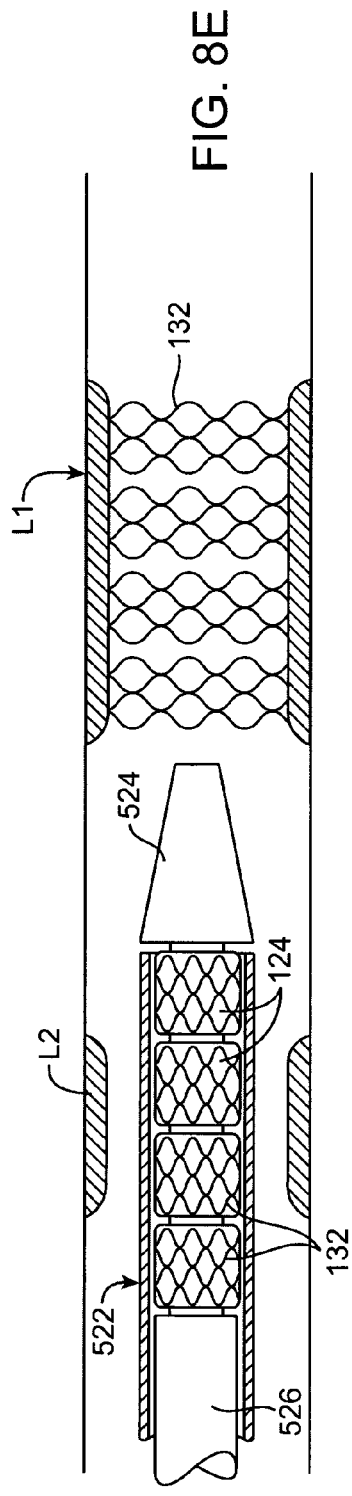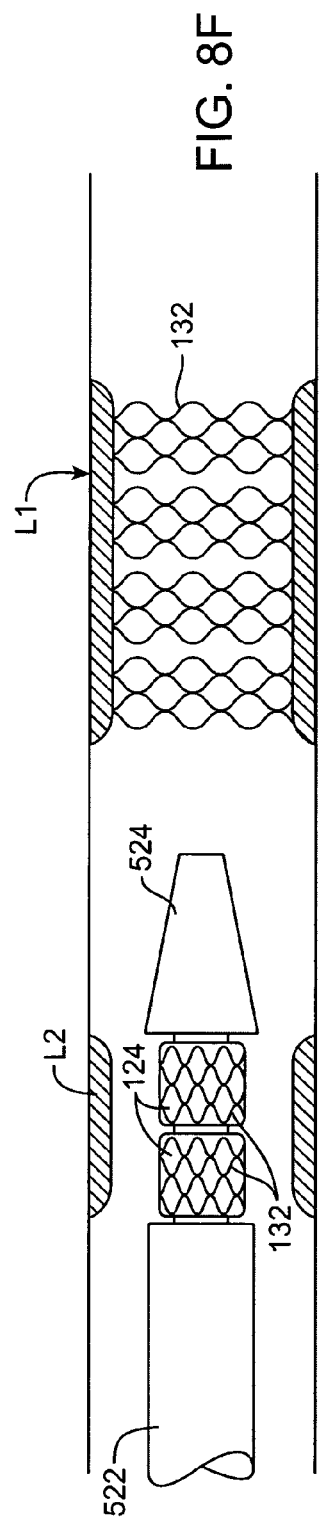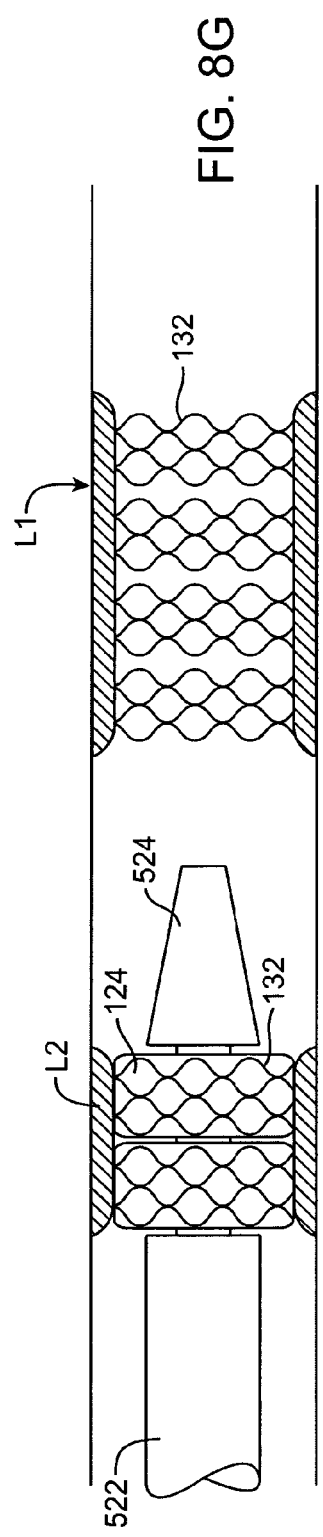

CUSTOM-LENGTH STENT DELIVERY SYSTEM WITH INDEPENDENTLY OPERABLE EXPANSION ELEMENTS

BACKGROUND OF THE INVENTION

The present invention relates generally to systems and methods for deploying stents at one or more treatment sites. More specifically, the invention relates to systems and methods for delivering multiple stents of various lengths to multiple treatment sites using a single device.

Stenting has become an increasingly important treatment option for patients with coronary artery disease. Stenting involves the placement of a tubular prosthesis within a diseased coronary artery to expand the arterial lumen and maintain the patency of the artery. Early stent technology suffered from problems with restenosis, the tendency of the coronary artery to become re-occluded following stent placement. However, improvements in stent design and the advent of drug-eluting stents have reduced restenosis rates dramatically. As a result, the number of stenting procedures being performed in the United States, Europe, and elsewhere has soared.

Stents are delivered to the coronary arteries using long, flexible vascular catheters typically inserted through a femoral artery. For self-expanding stents, the stent is simply released from the delivery catheter and it resiliently expands into engagement with the vessel wall. For balloon expandable stents, a balloon on the delivery catheter is expanded which expands and deforms the stent to the desired diameter, whereupon the balloon is deflated and removed.

Current stent delivery technology suffers from a number of drawbacks. For example, current stent delivery catheters are not capable of customizing the length of the stent in situ to match the size of the lesion to be treated. While lesion size may be measured prior to stenting using angiography or fluoroscopy, such measurements may be inexact. If a stent is introduced that is found to be of inappropriate size, the delivery catheter and stent must be removed from the patient and replaced with a different device of correct size.

Moreover, current stent delivery devices cannot treat multiple lesions with a single catheter. Current devices are capable of delivering only a single stent with a single catheter, and if multiple lesions are to be treated, a new catheter and stent must be introduced for each lesion to be treated.

For these and other reasons, stent delivery systems and methods are needed which enable the customization of stent length in situ, and the treatment of multiple lesions of various sizes, without requiring removal of the delivery catheter from the patient. Such stent delivery systems and methods should further be of minimal cross-sectional profile and should be highly flexible for endovascular positioning through tortuous vascular pathways. Ideally, such stent delivery systems would also allow for accurate and repeatable positioning of one or more stents in a desired position for deployment from a catheter in situ. At least some of these objectives will be met by the present invention.

BRIEF SUMMARY OF THE INVENTION

The invention provides stent delivery systems and methods that overcome the challenges outlined above and provide other advantages. The invention enables the delivery of multiple stents from a single catheter during a single intervention, wherein the length of each stent may be customized in situ. In preferred embodiments, the invention provides systems and methods for the delivery of segmented stents, which enable greater control and precision during stent deployment so that optimal stent position and inter-segment spacing are achieved.

In various embodiments, stent delivery systems and methods are used in stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. The stents and prostheses of the present invention commonly comprise a closed or, less preferably, an open lattice structure, and are typically formed from a malleable or elastic metal. When formed from a malleable metal, such as stainless steel, gold, platinum, titanium, and super alloys, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. The terms "stent" and "stent segments" refer broadly to all radially expansible stents, grafts, and other scaffold-like structures which are intended for deployment within body lumens.

In a first aspect of the invention, a stent delivery system for delivering a plurality of stent segments to at least one treatment site includes a catheter shaft having a proximal end and a distal end, a plurality of expandable members arranged axially along the catheter shaft near the distal end, a plurality of stent segments, and a selecting mechanism adapted for selecting one or more expandable members for expansion. In this embodiment, each expandable member is expandable independently of at least one other expandable member, and each expandable member has at least one stent segment positioned on it. One or more of the expandable members may be selectively expanded to deploy the one or more stent segments positioned thereon at the treatment site. It should be understood that, in many of the embodiments described herein, the invention will encompass either a plurality of separately constructed expandable elements each separately mounted to the catheter and operated independently of the others, or a single integral expandable element mounted to the catheter that has interior partitions to create a plurality of isolated independently-expandable compartments or segments.

In a typical embodiment, each of the plurality of expandable members and each of the plurality of stent segments is spaced apart from adjacent expandable members and stent segments, so that each stent segment can be expanded by each expandable member without interfering with adjacent stent segments. In some embodiments, each stent segment is crimped onto one of the expandable members so as to not be axially slidable along the expandable members. Alternatively, each stent segment may be axially slidable along the expandable members.

Some embodiments further include an inflation lumen in the catheter shaft and a plurality of apertures in communication with the inflation lumen, with each aperture being further in communication with at least one of the expandable members. In some embodiments, the selecting mechanism then comprises an isolating member movably disposed in the catheter shaft for isolating at least a first of the apertures from at least one other of the apertures. For example, the isolating member may comprise a first axially slidable seal. In one embodiment, the first axially slidable seal is coupled at or near a distal end of a first slidable shaft slidably coupled to the catheter shaft. In some embodiments, the catheter shaft has an inflation lumen therein, the first slidable shaft being disposed within the inflation lumen. Optionally, the selecting mechanism may further include a second isolating member for isolating a second aperture from at least one other aperture. Again, in one embodiment, the second isolating member comprises a second axially slidable seal. This second axially slidable seal may be coupled to a second shaft slidably coupled to the catheter shaft. In some embodiments, the first shaft defines a first lumen, and the second shaft is slidably disposed within the lumen. Optionally, a space between the first and second slidable tubular shafts may define an inflation lumen.

One alternative embodiment, includes multiple inflation lumens, each of which communicates with one of a plurality of expandable members or with an isolated section or compartment of a single expandable member. A proximal inflation lumen selector, usually including a manifold, is used to select which inflation lumen (or lumens) are used at any one time to expand one or more expandable members. In another alternative embodiment, rather than having multiple, separate expandable members, a stent delivery catheter may have a single, elongate expandable member with multiple septa dividing the balloon into multiple compartments.

Some embodiments further include at least a first axially movable sheath disposed over at least the expandable members and the stent segments. The system may optionally further include at least a second axially movable sheath disposed over part of the catheter shaft, the expandable members and the stent segments. In such an embodiment, the first sheath may be disposed proximally along the catheter shaft relative to the second sheath, and the first and second sheaths may be adapted to allow one or more selected stent segments to be deployed between the sheaths. In some embodiments, the second sheath is movable distally to allow for deployment of at least one stent segment and proximally to cover one or more of the expandable members from which at least one stent segment has been deployed. Optionally, the system may further include a pusher tube slidably disposed within the sheath and proximal to a proximal-most stent segment to advance and/or maintain an axial position of the stent segments relative to the expandable members.

In another aspect of the present invention, a stent delivery system for delivering a plurality of stent segments to at least one treatment site includes a catheter shaft having a proximal end and a distal end, a plurality of expandable members arranged axially along the catheter shaft near the distal end, a plurality of stent segments, and at least a first isolating member movably associated with the catheter shaft for selecting one or more expandable members for expansion. Each expandable member is expandable independently of at least one other expandable member, and each expandable member has at least one stent segment positioned on it. Thus, one or more of the expandable members may be selectively expanded to deploy the one or more stent segments positioned thereon at the treatment site. According to this aspect of the invention, the system may have any of the features described above.

In another aspect of the present invention, a method for delivering a plurality of stent segments to at least one treatment site first involves positioning a distal portion of a stent delivery catheter device at a first treatment site, the stent delivery catheter having a plurality of expandable members positioned thereto, and each of the expandable members having one or more stent segments positioned on it. The method then involves selecting one or more first expandable members for expansion and expanding only the one or more first expandable members to deploy at least a first stent segment at the first treatment site, while at least a second expandable member and at least a second stent segment on the stent delivery catheter remain unexpanded. In some embodiments, expanding only the one or more first expandable members comprises expanding two or more of the expandable members to deploy at least two of the stent segments.

Optionally, the method may further involve, after the step of expanding only the one or more first expandable members, expanding the second expandable member(s) to deploy the second stent segment(s). Such an embodiment may further comprise positioning the distal portion of the stent delivery catheter device at a second treatment site before expanding the second expandable member(s). In some embodiments, the method further includes, after the step of expanding the one or more first expandable members, axially repositioning the second stent segment from the second expandable member to a distal expandable member selected from the one or more first expandable members, and expanding the distal expandable member to deploy the second stent segment. Optionally, such a method may further comprise positioning the distal portion of the stent delivery catheter device at a second treatment site before expanding the second expandable member. In one embodiment, the second stent segment is repositioned by an axially movable pusher in the stent delivery catheter device. Some embodiments may further comprise selecting at least a third expandable member and expanding the third expandable member to deploy a third stent segment. Again, such a method may also include positioning the distal portion of the stent delivery catheter device at a third treatment site before expanding the third expandable member.

In some embodiments, selecting the first expandable member(s) comprises axially moving at least a first sealing member to seal off one or more first inflation apertures communicating with the first expandable member(s) from at least a second inflation aperture communicating with the second expandable member(s). For example, in one embodiment, axially moving the first sealing member comprises sliding a tubular shaft over an inner shaft. In such an embodiment, expanding may comprise introducing an inflation medium into the first expandable member(s) through an inflation lumen between the tubular shaft and the inner shaft. Such a method may also optionally involve axially moving the first sealing member to seal off the second inflation aperture(s) from at least a third inflation aperture communicating with one or more third expandable members, axially moving a second sealing member to seal off at least one of the first inflation apertures from the second inflation aperture(s), and expanding only the second expandable member(s) to deploy the second stent segment(s). In some embodiments, the first sealing member is coupled to a first shaft, the second sealing member is coupled to a second shaft, and axially moving the first and second sealing members comprises sliding the second shaft relative to the first shaft. For example, the first shaft may be tubular and the second shaft may be slidably disposed through the first shaft. In some embodiments, expanding comprises introducing an inflation medium into the second expandable member(s) through an inflation lumen between the first and second shafts.

Optionally, the method may further comprise axially moving a first sheath disposed over the expandable members and the plurality of stent segments, before the expanding step, to expose the first expandable member(s) and stent segment(s)

while covering the second expandable member(s) and second stent segment(s). The method may further involve contracting the first expandable member(s), moving the first sheath to cover the first expandable member(s), advancing the second stent segment(s) to be positioned on the first expandable member(s), moving the first sheath to expose the second expandable member(s), and expanding the second expandable member(s) to deploy at least the second stent segment(s).

In some embodiments, the method further includes positioning the distal portion of the stent delivery catheter device at a second treatment site before expanding the second expandable member(s). Such a method may also involve deflating the first expandable member(s), moving a second sheath to cover the first expandable member(s), moving the first sheath to expose the second expandable member(s) and the second stent segment(s), and expanding the second expandable member(s) to deploy the second stent segment(s) while the first expandable member(s) remain covered by the second sheath. Optionally, such a method may further involve positioning the distal portion of the stent delivery catheter device at a second treatment site before expanding the second expandable member(s)

Other aspects of the nature and advantages of the invention will become apparent from the following detailed description when taken in conjunction with the drawings.

BRIEF DESCRIPTION OF THE DRAWINGS

FIGS. 2A and 2B are partial cross-sectional side views of a distal end of a stent delivery catheter system, according to one embodiment of the present invention.

FIGS. 3A and 3B are partial cross-sectional side views of a distal end of a stent delivery catheter system, according to an alternative embodiment of the present invention.

FIGS. 7 and 7A are side and cross-sectional views, respectively, of a stent delivery catheter having multiple inflation lumens, according to one embodiment of the present invention.

FIGS. 8A-8G are partial cross-sectional side views of a distal end of a stent delivery catheter system, demonstrating a method for delivering multiple stent segments, according to one embodiment of the present invention.

DETAILED DESCRIPTION OF THE INVENTION

Figure 1:
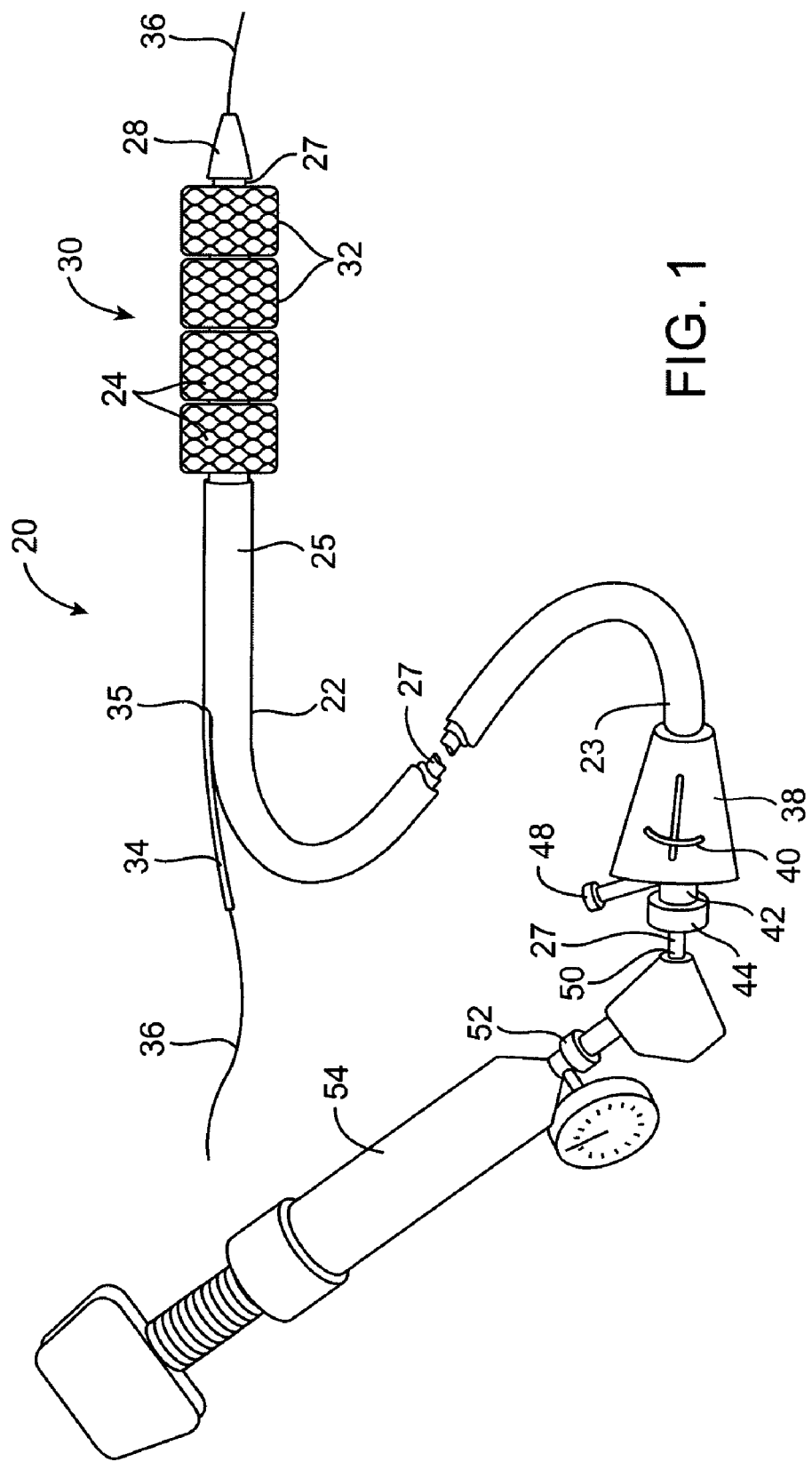
FIG. 1 is a perspective view of a stent delivery catheter system, according to one embodiment of the present invention.

A first embodiment of a stent delivery catheter system 20 according to the present invention is illustrated in FIG. 1. Stent delivery system 20 includes a catheter body 22 comprising an outer sheath 25 slidably disposed over an inner shaft 27. Multiple expandable members 24, preferably inflatable balloons (shown in an inflated configuration), are positioned to inner shaft 27 and are exposed by retracting sheath 25 relative to inner shaft 27. A tapered nosecone 28, composed of a soft elastomeric material to reduce trauma to the vessel during advancement of the device, is positioned distally of expandable members 24. One or more stents 30, comprising a plurality of separate or separable stent segments 32, is disposed on expandable members 24, such that each expandable member 24 has a stent segment 32 positioned on it for expansion therewith. A guidewire tube 34 is slidably positioned through a guidewire tube exit port 35 in sheath 25 proximal to expandable members 24. A guidewire 36 is positioned slidably through guidewire tube 34, expandable members 24, and nosecone 28 and extends distally thereof.

A handle 38 is positioned to a proximal end 23 of sheath 25 and includes an actuator 40 slidably positioned thereto for purposes described below. An adaptor 42 is positioned to the proximal end of handle 38 and provides a catheter port 44 through which inner shaft 27 is slidably positioned. A flush port 48 is positioned to the side of adaptor 42 through which a fluid such as saline can be introduced into the interior of catheter body 22. An annular seal (not shown) in catheter port 44 seals around inner shaft 27 to prevent fluid from leaking through catheter port 44. Optionally, a clamp (not shown) such as a threaded collar, can be positioned to catheter port 44 to lock inner shaft 27 relative to handle 38. Suitable handles for use with the present invention are further described in copending U.S. patent application Ser. No. 10/746,466, filed Dec. 23, 2003 (Attorney Docket No. 21629-002200US), which is hereby incorporated by reference.

Inner shaft 27 has a proximal end 50 to which is positioned an inflation adaptor 52. Inflation adaptor 52 is configured to be fluidly coupled to an inflation device 54, which may be any commercially available balloon inflation device such as those sold under the trade name "Indeflator™," available from Advanced Cardiovascular Systems of Santa Clara, Calif. Inflation adaptor 52 is in fluid communication with expandable member 24 via an inflation lumen (described below) in inner shaft 27 to enable inflation of expandable member 24.

Additional aspects of stent delivery devices suitable for use with the present invention are described in U.S. patent application Ser. No. 10/637,713 (Attorney-Docket No. 021629-000340US), filed Aug. 8, 2003, and assigned to the assignees of the present invention, the full disclosure of which is hereby incorporated by reference. In preferred embodiments, the geometry, construction, materials and other aspects of stent segments 32 may be similar to those described in copending U.S. patent application Ser. No. 10/738,666, filed Dec. 16, 2003 (Attorney Docket No. 21629-000510), which is hereby incorporated by reference. The present invention, however, includes a number of alternative and additional features, most significant of which are the multiple, individually inflatable, expandable members of the present invention and the various selection mechanisms employed in various embodiments to provide for individual expansion of the expandable members. These features will be described in further detail below.

Generally, the various embodiments of stent delivery catheter system 20 provide for independent expansion of expandable members 24 to independently deploy stent segments 24 at one or more treatment sites. By "independent expansion" and "independent deployment," it is meant that one or more expandable members 24 may be expanded to deploy one or more stent segments 32 while maintaining at least one other expandable member 24 and stent segment 32 thereon in an unexpanded, undeployed configuration. In some embodiments, as in FIG. 1, one or more sheaths 25 may cover unexpanded expandable members 24 and stent segments 32, while alternative embodiments do not include sheaths. Generally, the system includes some form of selection and/or isolating mechanism, for allowing a user to select one or more expandable members 24 for expansion. Using independently expandable members 24 allows for deployment of one or more stent segments 32 at a first site, followed by deployment of one or more additional segments 32 at a second site, and so on, for any number of lesions. In various alternative embodiments, a single, elongate expandable member having multiple inner septa or partitions to divide the expandable member into multiple separate chambers may be substituted for the multiple expandable members 24 shown in the FIG. 1 embodiment.

Lesions of various different lengths may be treated by selecting a desired number of expandable members 24 and associated stent segments 32 in situ to deploy at the lesion site. In various embodiments, a wide range of numbers, lengths, and types of stent segments 32 may be deployed, and a corresponding number, length, and type of lesions may be treated. Stent segments 32 have a length suitable for the anatomical location and characteristics of the lesion being treated, usually being about 2-30 mm in length, more typically being about 2-20 mm in length, and preferably being about 2-10 mm in length. In preferred embodiments, each expandable member 24 has an axial length suitable to accommodate one or more stent segments 32, usually having a length of about 3-65 mm, more typically about 3-25 mm in length, and prefereably about 4-15 mm, depending upon the length of stent segments 32 and the number of stent segments 32 mounted on each expandable member 24. Also the balloon length will be selected to provide the desired amount of balloon overhang (length of balloon not covered by stent) on the proximal and distal sides of each stent segment, usually being less than about 2 mm. Of course, if a single expandable member with separately inflatable compartments is used, its overall axial length would be longer, and the axial length of each compartment would correspond to the above ranges. Expandable members and stent segments of shorter or longer length are also possible without departing from the scope hereof.

Stent segments 32 may have any of a variety of common constructions, such as but not limited to those described in U.S. patent application Ser. No. 10/738,666, filed Dec. 16, 2003 (Attorney Docket No. 21629-000510), which was previously incorporated by reference. Stent segment 32 constructions may include, for example, closed cell constructions such as expansible ovals, ellipses, box structures, expandable diamond structures, expandable rhomboid structures, as well as other regular and irregular polygonal structures, etc. In addition, the closed cells may have complex slotted geometries, such as H-shaped slots, I-shaped slots, J-shaped slots, etc. Suitable open cell structures include zigzag structures, serpentine structures, and the like. Such conventional stent structures are well described in the patent and medical literature. Specific examples of suitable stent structures are described in the following U.S. Patents, the full disclosures of which are incorporated herein by reference: U.S. Pat. Nos. 6,315,794; 5,980,552; 5,836,964; 5,527,354; 5,421,955; 4,886,062; and 4,776,337.

Any number of stent segments 32 may be deployed from stent delivery catheter 20. Usually, the number of delivered stent segments 32 will be in the range from 2 to 50, more typically from 2 to 25, and preferably from 2 to 10. These correspond to overall deployed stent lengths of about 2-200 mm, more typically 4-100 mm, and preferably 4-60 mm. The multiple segments 32 may be deployed individually or in groups of two or more at a single location or at multiple spaced-apart locations in the body lumen or lumens.

Stent segments 32 are preferably constructed of a malleable metal so as to be plastically deformable by expandable members 24 as they are expanded to the desired diameter in the vessel. Alternatively, stent segments 32 may be formed of an elastic or super elastic shape memory material such as Nitinol so as to self-expand upon release into the vessel by retraction of sheath 25. Stent segments 32 may also be composed of polymers or other suitable biocompatible materials. In self-expanding embodiments, expandable member 24 may also be used for predilatation of a lesion prior to stent deployment or for augmenting the expansion of the self-expanding stent segments.

In some embodiments, stent segments 32 are coated, impregnated, infused or otherwise coupled with one or more drugs that inhibit restenosis, such as Rapamycin, Everolimus, Paclitaxel, analogs, prodrugs, or derivatives of Rapamycin, Everolimus or Paclitaxel, or other suitable agent(s), preferably carried in a durable or bioerodable polymeric carrier. Alternatively, stent segments 32 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics and/or stem cells. Such materials may be coated over all or a portion of the surface of stent segments 32, or stent segments 32 may include apertures, holes, channels, or other features in which such materials may be deposited.

Stent segments 32 are preferably completely separate from one another without any interconnections, but alternatively may have couplings between two or more adjacent segments 32 which permit flexion between the segments 32. As a further alternative, one or more adjacent stent segments 32 may be connected by separable or frangible couplings that are separated prior to or upon deployment, as described in copending application Ser. No. 10/306,813, filed Nov. 27, 2002 (Attorney Docket No. 21629-000320), which is incorporated herein by reference.

Sheath 25 may have any suitable shape, length, cross-sectional diameter, material thickness, and the like and may be made of any suitable material or combination of materials. In one embodiment, for example, sheath 25 may have a length selected to extend over all of expandable members 24, in one embodiment being between about 100 cm and about 125 cm. Sheath 25 may be constructed of any of a variety of biocompatible materials, such as but not limited to a polymer such as PTFE, FEP, polyimide, or Pebax, may be reinforced with a metallic or polymeric braid to resist radial expansion of expandable members 24, and/or the like. Expandable members 24 comprise expandable balloons, which may be formed of a semi-compliant polymer such as Pebax, Nylon, polyurethane, polypropylene, polytetrafluoroethylene (PTFE), or other suitable polymer. Stent segments 32 are positioned at fixed positions on expandable members 24.

Referring now to FIGS. 2A and 2B, in one embodiment, a distal end of stent delivery catheter 120, shown in partial cross-section, includes an inner catheter shaft 127, a guidewire 136 extending through inner shaft 127, an outer catheter shaft 156, a distal nosecone 128, multiple expandable members 124, multiple stent segments 132 and a slidable tubular member 160 disposed over inner catheter shaft 127 and coupled near its distal end with a sealing member 162. Outer catheter shaft 156 forms a catheter shaft lumen 166 and includes multiple inflation apertures 158, each of which is in fluid communication with catheter shaft lumen 166 and the interior space of one expandable member 124. An inflation lumen 164 is formed by a space between slidable tubular member 160 and inner catheter shaft 127.

Sealing member 162 may be comprised of a resilient or rigid material suitable for forming a seal between itself and the inner surface of outer catheter shaft 156, such as an elastomer or other resilient material. Thus, when an inflation medium, such as saline, is passed through inflation lumen 164, into catheter shaft lumen 166, sealing member confines the inflation medium to the portion of catheter shaft lumen 166 distal to it and to any expandable members 124 distal to it. By moving slidable tubular member 160 axially, as shown in FIGS. 2A and 2B, a number of expandable members 124, ranging from one to as many as desired, may be selected for inflation and expansion. In FIG. 2B, the two distal-most expandable members 124 have been selected and expanded via inflation medium (solid-tipped arrows), and the two distal-most stent segments 132 have thus been expanded and deployed. In a subsequent deployment, as will be described more fully below, slidable tubular member 160 may be moved again to change the position of sealing member 162, and one or more additional expandable members 124 may be inflated to deploy one or more additional stent segments 132. One or more expandable members 124 and/or stent segments 132 thereon may have different expanded diameter, length, geometry, material, coatings and/or other features than other expandable members 124 or stent segments 132. This way, one or more stent segments 132 may be selected to have the optimum size, shape, material, elution profile, and therapeutic effect for the lesion or part of the lesion being treated.

In contrast to the embodiment shown in FIG. 1, the embodiment in FIGS. 2A and 2B does not include a sheath. In an embodiment without a sheath, stent segments 132 may be crimped or otherwise coupled with expandable members 124 relatively tightly or snugly, so that they remain coupled to expandable members 124 during insertion of catheter 120 into a blood vessel. Embodiments without sheaths have the advantages of a smaller profile and reduced stiffness and complexity. Additionally, if stent segments 132 are fixed or crimped onto expandable members 124, catheter 120 does not require a pusher member or other mechanism for advancing stent segments 132 or holding them in place while a sheath is retracted. At least one alternative embodiment, described further below, does include a sheath, which may be advantageous for protecting stent segments 132 during advancement of the catheter and for other reasons. In embodiments having sheaths, stent segments may be axially slidable along the expandable members, such that segments may be advanced to take up the positions from which stent segments have been deployed.

Referring now to FIGS. 3A and 3B, an alternative embodiment of a stent delivery catheter 220 includes many of the features described above and also includes an inner tubular member 268 coupled with a distal sealing member 270 and an outer tubular member 260 coupled with a proximal sealing member 262, with an inflation lumen 264 formed between the two tubular members 260, 268. Inner tubular member 268 is disposed between inner catheter shaft 127 and outer tubular member 260 and extends distally out of the latter. Both outer tubular member 260 and inner tubular member 268 are axially slidable relative to each other and to inner catheter shaft 127. Thus, each tubular member 260, 268 may be moved separately to position sealing members 262, 270 to isolate one or more expandable members 124 for expansion.

As shown in FIG. 3A, tubular members 260, 268 may first be used to position sealing members 262, 270 to isolate a distal-most expandable member 124 for expansion (or any other desired expandable member or members 124), thus deploying a distal-most stent segment 132. After stent segment 132 is deployed, expandable member 124 is allowed to deflate. As shown in FIG. 3B, outer tubular member 260 and inner tubular member 268 may then be moved proximally to allow distal sealing member 270 and proximal sealing member 262 to isolate one or more additional expandable members 124 for expansion, thus deploying additional stent segments 132. One advantage of this embodiment is that the combination of proximal sealing member 262 and distal sealing member 270 allows for deployment of additional stent segments 132 without inflating expandable members 124 from which segments 132 have already been deployed. For example, as shown in FIG. 3B, when the additional stent segments 132 are deployed, the distal-most expandable member 124 does not expand, because distal sealing member 270 prevents inflation medium from passing into it. Of course, outer and inner tubular members 260, 268 and proximal and distal sealing members 262, 270 may be moved in any desired combination to allow for deployment of stent segments 132 in any desired number, configuration or pattern. For example, in an alternative embodiment, one or more proximal stent segments 132 may be deployed before one or more distal stent segments 132, stent segments 132 may be deployed one at a time from distal to proximal, groups of stent segments 132 may deployed all at once, or the like. Thus, the method demonstrated by FIGS. 3A and 3B is but one example of a number of possible deployment methods. Moreover, an annular lumen within inner tubular member 268 may be used to deliver inflation fluid to any expandable members 124 distal to distal sealing member 270, independently of that delivered via outer tubular member 260. This enables different expandable members 124 to be inflated at different pressures and/or diameters than other expandable members 124, even at the same treatment site.

Figure 4:
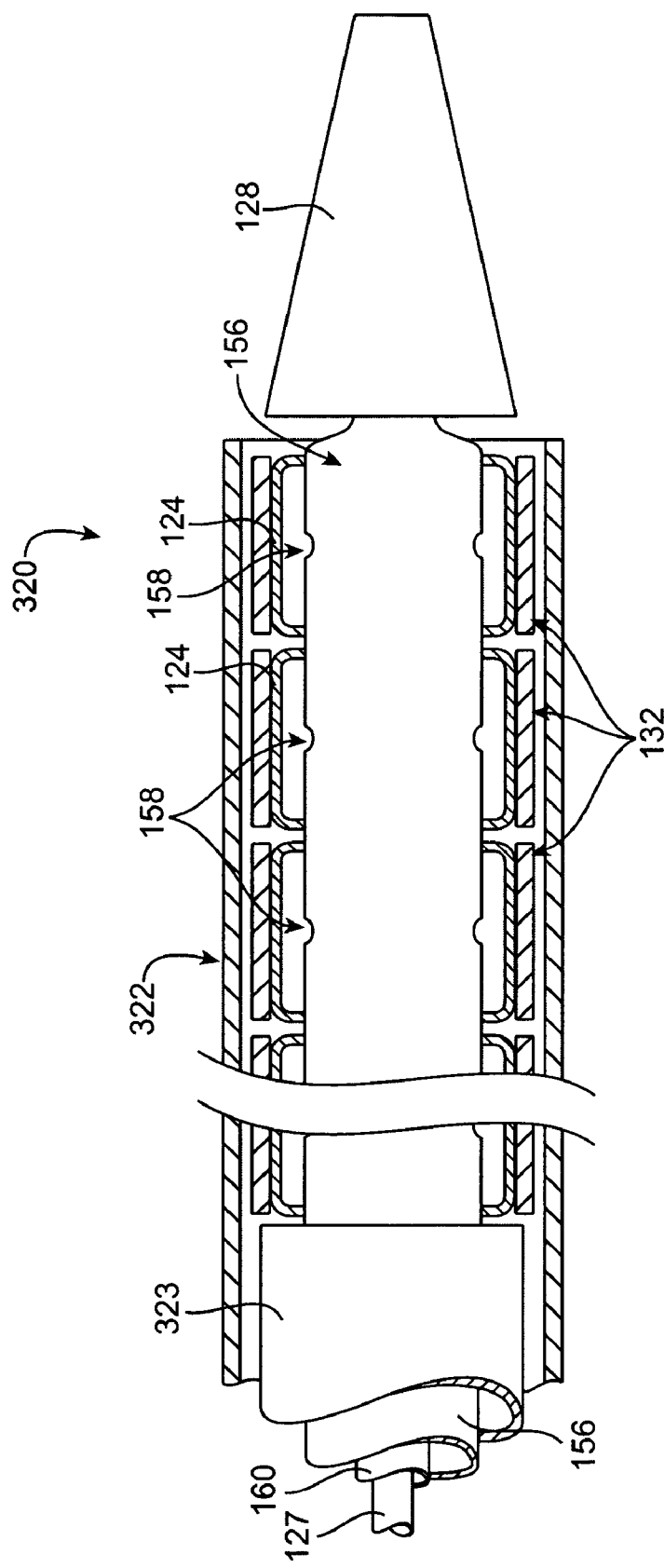
FIG. 4 is a partial cross-sectional side view of a distal end of a stent delivery catheter system including a sheath, according to another alternative embodiment of the present invention.

With reference now to FIG. 4, in an alternative embodiment, a stent delivery catheter 320 includes a sheath 322 disposed over expandable members 124 and stent segments 132. Sheath 322 typically surrounds stent segments 132 during advancement and positioning of catheter 320, thus protecting segments 132 from possible damage, and then is retracted to expose a desired number of segments 132 for deployment. A single inflation lumen within outer catheter shaft 156 communicates with each expandable member 124 via ports 158. One or more sliding seals (not shown) may optionally be provided within outer catheter shaft 156 to isolate selected ports 158 from other ports 158. A slidable pusher tube 323 is disposed proximal to the proximal-most stent segment 132 to maintain the position of segments 132 curing retraction of sheath 322. In some embodiments, pusher tube 323 may also be used to advance stent segments 132 distally along expandable members 124. In such embodiments, segments 132 are more loosely placed over expandable members 124, so as to be slidable along them. Exemplary embodiments of stent delivery catheters having sheaths are described in further detail in U.S. patent application Ser. No. 10/637,713 (Attorney-Docket No. 021629-000340US), which was previously incorporated by reference.

In use, sheath 322 is typically positioned over stent segments 132 during advancement of catheter 320 to a treatment site. Sheath 322 is then retracted proximally to expose a desired number of stent segments 132, while pusher tube 323 is maintained in a fixed position to prevent stent segments 132 from moving proximally along expandable members 124 while the sheath is retracted. Inflation fluid is then delivered through the inflation lumen in outer catheter shaft 156 to inflate those expandable members 124 exposed outside of sheath 322. Sheath 322 constrains the remaining expandable members 124 and associated stent segments 132 from expanding. After the exposed stent segments 132 are deployed, the expandable members 124 used to deploy those stent segments 132 are deflated, sheath 322 is then repositioned over the deflated expandable members 124, and pusher tube 323 may be used to advance undeployed stent segments 132 over the deflated expandable members 132. At a second treatment site, the process may be repeated, deploying the same or a different number and/or length of stent segments 132.

Figure 5A:
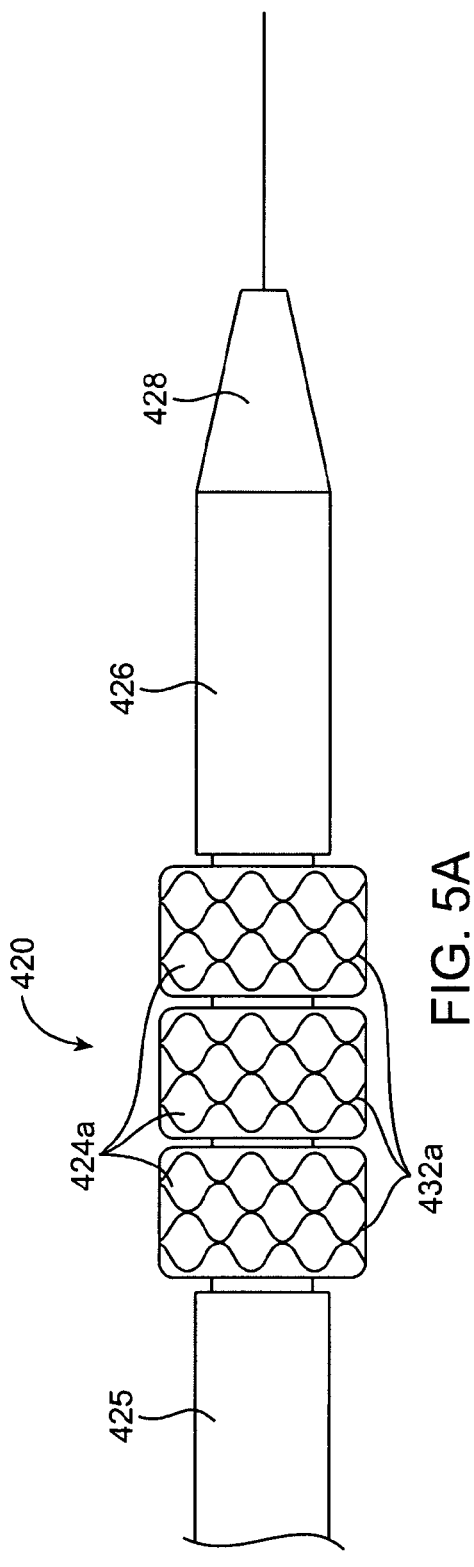
FIGS. 5A and 5B are side views of a stent delivery catheter system having two sheaths, demonstrating deployment of two variously sized stent segments, according to one embodiment of the present invention.
Figure 5B:
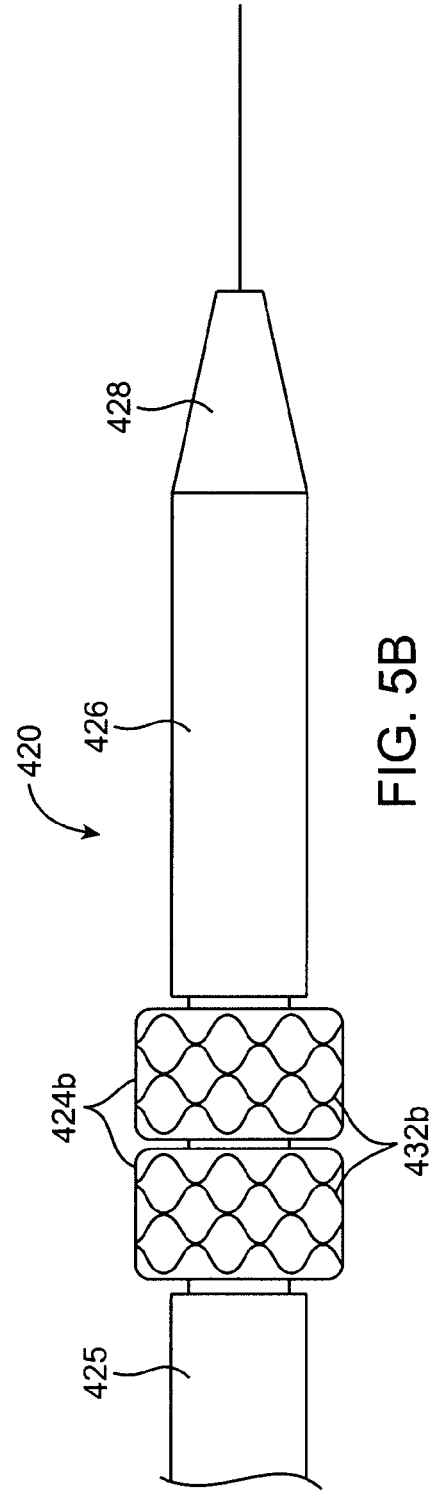

In an alternative embodiment, and with reference now to FIGS. 5A and 5B, a stent delivery catheter device 420 may include a proximal sheath 425 and a distal sheath 426. Proximal sheath 425 and distal sheath 426 are slidably disposed over expandable members 424, and stent segments 432 disposed thereon, when in an unexpanded configuration. Distal sheath 426 is coupled with nosecone 428, and nosecone 428 is coupled with a distal sheath actuator (not shown) slidably disposed within catheter device 420, which is used to axially move distal sheath 426 and nosecone 428 relative to expandable members 424. Proximal sheath 425 extends up to the proximal end of distal sheath 426 from the proximal end of catheter 420 and is slidably disposed over expandable members 424. In various embodiments, proximal sheath 425 may be movable proximally, distally or both. For example, proximal sheath 425 may sometimes be retracted proximally to expose one or more expandable members 424 and one or more stent segments 432 between the two sheaths 425, 426, but in some embodiments may also be advanced distally to cover one or more expandable members 424 and stent segments 432 thereon.

In use, distal sheath 426 may be moved distally to expose a first expandable member 424a and one or more stent segments 432a disposed thereon, as in FIG. 5A, and may then be repositioned proximally to expose a second plurality of expandable members 424b and one or more stent segments 432b disposed thereon, as in FIG. 5B. Following deployment of stent segments 432a from expandable members 424a, distal sheath 426 may be positioned over expandable members 424a to constrain them from expansion while expandable members 424b are expanded. In this embodiment, as with others described herein, the plurality of expandable members 424 may be replaced by one or more longer expandable members with a plurality isolated, partitioned compartments or segments therein that may be independently expanded.

Examples of stent delivery devices having multiple sheaths, which may be adapted for use with various embodiments of the present invention are described in copending U.S. patent application Ser. No. 10/686,025 (Attorney Docket No. 21629-002000US), filed Oct. 14, 2003, which is hereby incorporated by reference.

FIGS. 5A and 5B demonstrate one way in which stent delivery catheter device 420 of the present invention may be used to deliver stents having different lengths and/or different numbers of stent segments 432. In FIG. 5A, distal sheath 426 and proximal sheath 425 are positioned to expose a set of two expandable members 424a and two stent segments 432a. In FIG. 5B, distal sheath 426 and proximal sheath 425 are positioned to expose a different, more proximal expandable member 424b and a corresponding stent segment 432b thereon. Of course, any number of different stent segments may be positioned in fixed positions on expandable members 424, and proximal and distal sheaths 425, 426 may be positioned in any number of combinations to allow a physician to place various stent segments 432 at various locations to treat multiple lesions.

Figure 6:
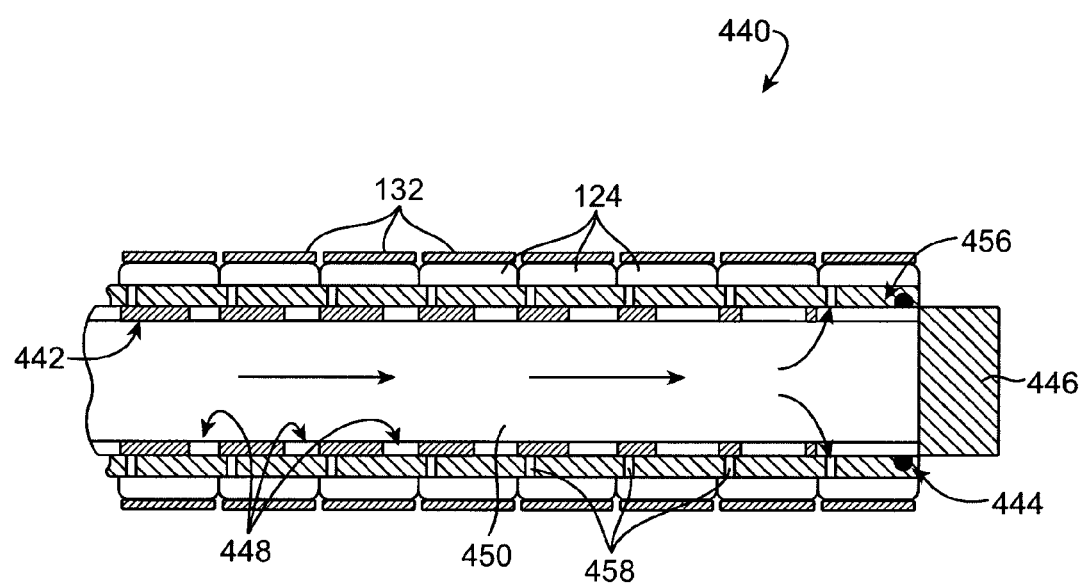
FIG. 6 is a cross-sectional side view of a distal end of a stent delivery catheter system having a movable inner tube with inflation slots, according to another alternative embodiment of the present invention.

With reference now to FIG. 6, a distal portion of an alternative embodiment of a stent delivery catheter device 440 is shown in cross section. This embodiment again includes multiple expandable members 124 and multiple stent segments 132, with each expandable member 124 having one segment 132 positioned on it. Again, in alternative embodiments, catheter device 440 may include one expandable member divided by multiple septa into multiple chambers. Also in alternative embodiments, two or more stent segments 132 may be positioned on each expandable member 124. Many alternative embodiments and combinations may be used.

In the embodiment shown in FIG. 6, expandable members 124 are disposed axially along an outer catheter shaft 456, which includes multiple, fixed inflation apertures 458, each aperture 458 in communication with the interior space of one expandable member 124. An axially slidable inner inflation tube 442 is slidably disposed within outer catheter shaft 456 and includes multiple inflation slots 448 of gradually increasing axial length, which are in fluid communication with an inflation lumen 450 in the center of tube 442, and a distal cap 446. A seal 444, such as an elastomeric O-ring, may be included to seal any space between outer shaft 456 and inner tube 442 at or near their distal ends. Optionally, such seals 444 may be provided between each inflation slot 448 to eliminate fluid communication therebetween.

In the embodiment shown, inflation fluid (solid-tipped arrows), such as saline, is passed into inflation lumen 450. When inner tube 442 is positioned as far distally as possible, only one movable inflation slot 448 is aligned with one fixed inflation aperture 458, thus allowing only a distal-most expandable member 124 to expand. All other fixed inflation apertures 458 are covered by solid portions of inner tube 442, so that inflation fluid cannot pass into the other expandable members. If inner tube 442 is moved more proximally, other movable slots 448 align with other fixed inflation apertures 458, thus allowing for expansion of additional expandable members 124. As with other embodiments described above, this embodiment may be used to expand and deploy a selected number of stent segments 132 to treat lesions of various lengths. The embodiment of FIG. 6 may optionally include one or more sheaths slidably disposed over stent segments 132 and a pusher adapted to advance stent segments 132 distally over expandable members 124, as shown in FIGS. 4, 5A and 5B above.

FIGS. 7 and 7A show another embodiment of a stent delivery catheter device 620 in side and cross-sectional views, respectively. In this embodiment, catheter device 620 includes a catheter shaft 626 having multiple inflation lumens 640 running axially along its length. The distal end of catheter device 620 includes a nosecone 628 and multiple inflation ports 634, with each inflation lumen 640 ending in one inflation port 634, or a set of inflation ports 634, that communicate (s) with a single expandable member 624. Each expandable member 624, in turn has two stent segments 632 disposed thereon, although in alternative embodiments one segment 632 or more than two segments 632 may be disposed on each expandable member 624. The proximal end of catheter device 620 includes a handle, as previously described in reference to FIG. 1, and an inflation adaptor 622 for connecting to a device for introducing inflation medium into inflation lumens 640. The proximal end of catheter device 620 also includes a manifold 649 communicating with each inflation lumen 640 and with a primary inflation lumen extending through handle 638 from inflation adaptor 622. An inflation lumen selector 650 allows a user to select which lumen (or lumens) will receive inflation medium (such as saline) during a given deployment of stent segment(s) 632. Each position of selector 650 may correspond with a single inflation lumen 640 and single expandable member 624, or in alternative embodiments each selector 650 may correspond with multiple inflation lumens 640 and multiple expandable members 624. For example, a physician may choose to inflate selected expandable members 624 associated with one or more inflation lumens 640 by positioning selector 650 at a first numbered position during a first deployment at a first treatment site, and then may select a different inflation lumen 640 corresponding to a different numbered position of selector 650 for a second deployment at a second site. Of course, any number of inflation lumens 640 may be included, in various embodiments, and various inflation lumen selectors 650 may be included at the proximal end of catheter device 620, such as manifolds, switches or the like.

Referring now to FIGS. 8A-8G, one embodiment of a method for deploying multiple stent segments 132 at two lesions L1, L2 in a vessel V is shown schematically. As demonstrated in FIG. 8A, to begin a stent deployment, a distal end of a stent delivery catheter device 520 is advanced to a desired location in the vessel V, within a first lesion L1, with an atraumatic nosecone 524 helping prevent damage to the vessel during advancement. A sheath 522 is then retracted proximally (solid-tipped arrow). In FIG. 8B, sheath 522 has been retracted to expose four expandable members 124, each carrying one stent segment 132. The four exposed expandable members 124 are then inflated with inflation fluid, as shown in FIG. 8C, thus expanding and deploying stent segments 132. As shown in FIG. 8D, the four expandable members 124 are then deflated, leaving the deployed stent segments in place within the first lesion L1.

FIG. 8E shows sheath 522 in cross section, to demonstrate that as a next step, expandable members 124 that were used in the first deployment may be retracted back into sheath 522 or sheath may be advanced over the deflated expandable members 124. A pusher tube 526 may then be used to advance stent segments 132 axially along expandable members 124 to cover the four already-used, distal-most expandable members 124 with stent segments 132. Before, after or during these steps, stent delivery catheter 520 may be repositioned within a second lesion L2, and the method just described may be repeated. As shown in FIG. 8F, sheath 522 may now be retracted to expose two expandable members 124 and stent segments 132. Expandable members 124 may then be expanded, as in FIG. 8G, to deploy the two stent segments 132 in the second lesion L2. Using this technique, any number of stent segments may be deployed in any combinations to treat any number of lesions having any combinations of lengths. In some embodiments, in fact, multiple, differently sized lesions in multiple vessels may be treated.

While the above is a complete description of the preferred embodiments of the invention, various alternatives, modifications, additions, and substitutions are possible without departing from the scope thereof, which is defined by the claims.

What is claimed is:

1. A stent delivery system for delivering a plurality of stent segments to at least one treatment site, the system comprising:
   a catheter shaft having a proximal end and a distal end;
   a plurality of expandable members arranged axially along the catheter shaft near the distal end, each expandable member being expandable independently of at least one other expandable member; and
   a plurality of stent segments, each expandable member having at least one stent segment positioned thereon; wherein one or more of the stent segments may be deployed independently of one or more other of the stent segments;
   a selecting mechanism adapted for selecting one or more expandable members for expansion independently of the other expandable members
   an inflation lumen in the catheter shaft; and
   a plurality of apertures in communication with the inflation lumen, each aperture being further in communication with at least one of the expandable members,
   wherein the selecting mechanism comprises an first isolating member movably disposed in the catheter shaft for isolating at least a first of the apertures from at least one other of the apertures and a second isolating member for isolating a second aperture from at least one other aperture.

2. A system as in claim 1, wherein the second isolating member comprises a second axially slidable seal.

3. A system as in claim 2, wherein the second axially slidable seal is coupled to a second shaft slidably coupled to the catheter shaft.

4. A system as in claim 3, wherein the first isolating member is coupled to an outer tubular member, the outer tubular member defining a first lumen, and
   wherein the second shaft is slidably disposed within the first lumen.

5. A system as in claim 4, wherein a space between the outer tubular member and the second shaft defines the inflation lumen.

6. A stent delivery system for delivering a plurality of stent segments to at least one treatment site, the system comprising:
   a catheter shaft having a proximal end and a distal end;
   an inflation lumen in the catheter shaft;
   a plurality of expandable members arranged axially along the catheter shaft near the distal end, each expandable member being expandable independently of at least one other expandable member;
   a plurality of apertures in communication with the inflation lumen, each aperture being further in communication with at least one of the expandable members;
   a plurality of stent segments, each expandable member having at least one stent segment positioned thereon;
   a first isolating member movably associated with the catheter shaft for selecting one or more expandable members for expansion, wherein one or more of the expandable members may be selectively expanded to deploy the one or more stent segments positioned thereon at the treatment site,
   wherein the first isolating member is movably disposed in the catheter shaft for isolating at least a first of the apertures from at least one other of the apertures; and
   wherein the first isolating member comprises a first axially slidable seal; and a second isolating member for isolating a second aperture from at least one other aperture.

7. A system as in claim 6, wherein the second isolating member comprises a second axially slidable seal.

8. A system as in claim 7, wherein the second axially slidable seal is coupled to a second shaft slidably coupled to the catheter shaft.

9. A system as in claim 8, wherein the first isolating member is coupled to an outer tubular member, the outer tubular member defining a first lumen, and
   wherein the second shaft is slidably disposed within the first lumen.

10. A system as in claim 9, wherein a space between the first isolating member and the second shaft defines the inflation lumen.

* * * * *